US010941090B2

United States Patent
Jungong et al.

(10) Patent No.: US 10,941,090 B2
(45) Date of Patent: Mar. 9, 2021

(54) PROCESSES FOR PRODUCING TRIFLUOROIODOMETHANE USING METAL TRIFLUOROACETATES

(71) Applicant: Honeywell International Inc., Morris Plains, NJ (US)

(72) Inventors: Christian Jungong, Depew, NY (US); Haiyou Wang, Amherst, NY (US); Terris Yang, East Amherst, NY (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 16/797,707

(22) Filed: Feb. 21, 2020

(65) Prior Publication Data

US 2020/0283359 A1 Sep. 10, 2020

Related U.S. Application Data

(60) Provisional application No. 62/813,500, filed on Mar. 4, 2019.

(51) Int. Cl.
*C07C 17/361* (2006.01)
*C07C 19/16* (2006.01)

(52) U.S. Cl.
CPC ............ *C07C 17/361* (2013.01); *C07C 19/16* (2013.01); *C07C 2523/06* (2013.01); *C07C 2523/745* (2013.01)

(58) Field of Classification Search
CPC .. C07C 17/361; C07C 19/16; C07C 2523/745
See application file for complete search history.

(56) References Cited

U.S. PATENT DOCUMENTS

2006/0122440 A1    6/2006  Mukhopadhyay et al.

FOREIGN PATENT DOCUMENTS

| CN | 101219925 A | 7/2008 |
| CN | 102992943 A | 3/2013 |

OTHER PUBLICATIONS

Hongying et al, Preparation of trifluoroiodomethane, CN 102992943 machine translation, Jun. 2015.*
Exner et al., "Iron-Catalyzed Decarboxylation of Trifluoroacetate and Its Application to the Synthesis of Trifluoromethyl Thioethers", Chem. Eur. J., 2015, vol. 21, pp. 17220-17223.
Haszeldine, R. N. (1951). 124. The Reactions of Metallic Salts of Acids with Halogens. Part I. The Reaction of Metal Trifluoroacetates with Iodine, Bromine, and Chlorine. Journal of the Chemical Society, pp. 584-587.
International Search Report and Written Opinion received for PCT Patent Application No. PCT/US2020/020731, dated Jun. 29, 2020, 11 pages.

* cited by examiner

*Primary Examiner* — Jafar F Parsa
(74) *Attorney, Agent, or Firm* — Faegre Drinker Biddle & Reath LLP

(57) ABSTRACT

The present disclosure provides a process for producing trifluoroiodomethane. The process includes providing a metal trifluoroacetate, an iodine source, a metal catalyst, and a solvent, and reacting the metal trifluoroacetate and the iodine source in the presence of the metal catalyst and the solvent to produce trifluoroiodomethane. The metal catalyst includes at least one selected from the group of ferrous chloride and zinc (II) iodide.

20 Claims, 1 Drawing Sheet

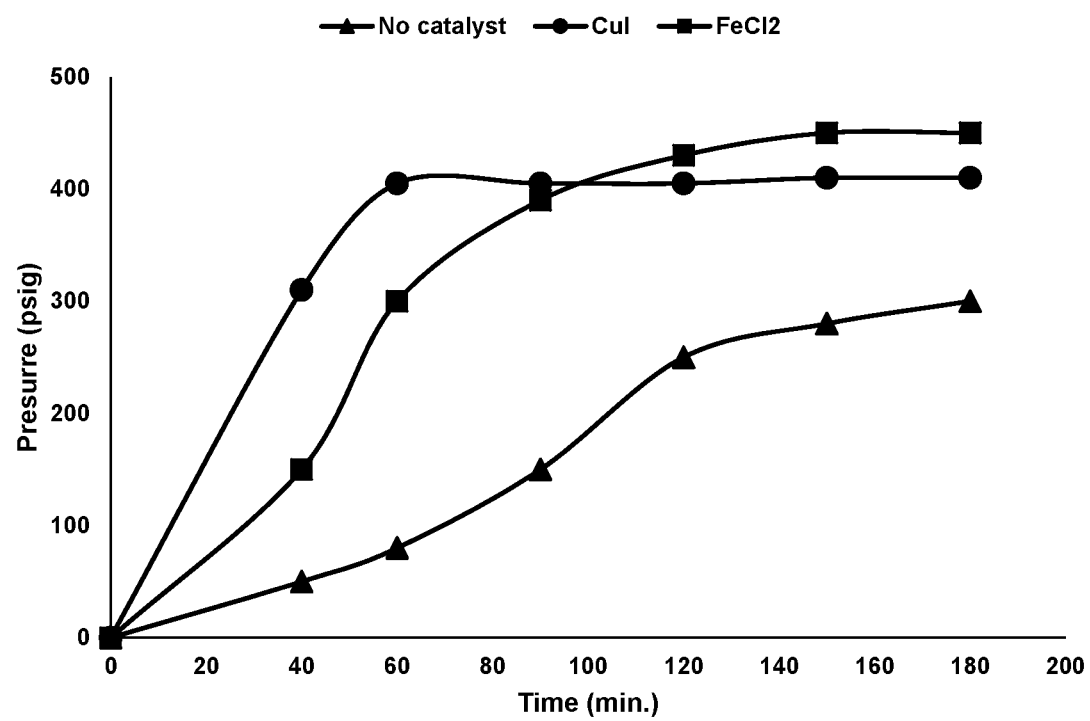

PROCESSES FOR PRODUCING TRIFLUOROIODOMETHANE USING METAL TRIFLUOROACETATES

CROSS-REFERENCE TO RELATED APPLICATIONS

This application is a U.S. Nonprovisional Application which claims priority to Provisional Application No. 62/813,500, filed Mar, 4, 2019, which is incorporated herein by reference in its entirety.

FIELD

The present disclosure relates to processes for producing trifluoroiodomethane ($CF_3I$). Specifically, the present disclosure relates to methods to produce trifluoroiodomethane from metal trifluoroacetates.

BACKGROUND

Trifluoroiodomethane ($CF_3I$) is a useful compound in commercial applications, as a refrigerant or a fire suppression agent, for example. Trifluoroiodomethane is an environmentally acceptable compound with a low global warming potential and low ozone depletion potential. Trifluoroiodomethane can replace more environmentally damaging materials.

Methods of preparing trifluoroiodomethane from metal trifluoroacetates and iodine are known. For example, R. N Haszeldine, *Reactions of metallic salts of acids with halogens. Part I. The reaction of metal trifluoroacetates with iodine, bromine, and chlorine*, 124 J. Chem. Soc. (1951) discloses the decarboxylative iodination of metal trifluoroacetates ($CF_3COOM$) in the presence of iodine to make trifluoroiodomethane. The process by R. N Haszeldine is performed in a sealed tube or stainless-steel autoclave in which the metal trifluoroacetate and elemental iodine are heated together in the absence of a solvent to make trifluoroiodomethane. In another example, Chinese Patent CN102992943B discloses the reaction of metal trifluoroacetates and elemental iodine in the liquid phase to produce trifluoroiodomethane, carbon dioxide, and metal iodide.

Yet in other examples, metal catalysts have been used in the liquid phase to promote trifluoromethylation reactions of aromatic- and alkyl halides, using metal trifluoroacetates as the trifluoromethylating agents. For instance, Chun Song et al, *Progress in Copper-Catalyzed Trfifluoromethylation*, 14 Beilstein J. Org. Chem, 2018, 155-181 discloses the trifluoromethylation of aryl iodides using potassium trifluoroacetate as the trifluoromethylating agent. In the process, two mole equivalents of copper (I) iodide with respect to the amount of aryl iodide were used. Notably, in other examples, copper (I) iodide was only used in sub-stoichiometric amounts. While the use of the metal catalyst will reduce reaction time, assure completion of the reaction, and produce high yields, copper (I) iodide is a relatively expensive catalyst.

Thus, there is a need to develop catalysts that are more efficient and economical in the production of trifluoroiodomethane from metal trifluoroacetates.

SUMMARY

The present disclosure provides processes for producing trifluoroiodomethane by reacting a metal trifluoroacetate with an iodine source in the presence of a metal catalyst including ferrous chloride ($FeCl_2$) and/or zinc (II) iodide ($ZnI_2$).

In one form thereof, the present disclosure provides a process for producing trifluoroiodomethane. The process includes providing a metal trifluoroacetate, an iodine source, a metal catalyst, and a solvent, and reacting the metal trifluoroacetate and iodine source in the presence of the metal catalyst and the solvent to produce trifluoroiodomethane. The metal catalyst includes at least one selected from the group of ferrous chloride and zinc (II) iodide.

In one form thereof, the present disclosure provides a process for producing trifluoroiodomethane. The process includes mixing a metal trifluoroacetate, an iodine source, a metal catalyst, and a solvent; and heating the metal trifluoroacetate, the iodine source, the metal catalyst, and the solvent to react the metal trifluoroacetate and iodine source to produce trifluoroiodomethane and a metal salt. The metal catalyst includes at least one selected from the group of ferrous chloride and zinc (II) iodide.

The above mentioned and other features of the disclosure, and the manner of attaining them, will become more apparent and will be better understood by reference to the following description of embodiments taken in conjunction with the accompanying drawings.

DESCRIPTION OF THE DRAWING

The FIGURE illustrates the pressure in a reactor over time for batch syntheses of trifluoroiodomethane corresponding to Examples 1-3 below. The FIGURE compares a synthesis using a ferrous chloride catalyst to a synthesis using a copper (I) iodide catalyst, and to a synthesis using no catalyst.

DETAILED DESCRIPTION

The present disclosure provides a liquid phase process for the manufacture of trifluoroiodomethane ($CF_3I$) from a metal trifluoroacetate ($CF_3COOM$) and an iodine source, such as iodine ($I_2$), iodine monochloride (ICl), or iodine pentafluoride ($IF_5$) by decarboxylative iodination according to Equation 1 below:

$$CF_3COOM + I-X_{(z)} \rightarrow CF_3I + CO_2 + MX \qquad \text{Eq. 1:}$$

where M is an alkali metal, such as lithium, potassium, or sodium, or an alkaline earth metal, such as calcium or magnesium; X is a halogen, such as fluorine, chlorine, bromine, or iodine; and Z is an integer. Thus, the metal trifluoroacetate may be at least one selected from the group of lithium trifluoroacetate, potassium trifluoroacetate, sodium trifluoroacetate, calcium trifluoroacetate, and magnesium trifluoroacetate.

The reaction is carried out with a metal catalyst. The use of a metal catalyst provides advantages in the production of trifluoroiodomethane. In general, copper(I) iodide (CuI) catalyzed trifluoromethylation reactions involving metal trifluoroacetates are believed to function through a single-electron transfer mechanism. However, it is generally used in stoichiometric amounts. The high cost of copper(I) iodide, in conjunction with the amount needed, make it desirable to find other catalysts capable of promoting decarboxylative iodination of metal trifluoroacetates for the formation of $CF_3I$.

Catalysts useful for carrying out the reaction in the liquid phase have been found to include ferrous chloride ($FeCl_2$) and zinc (II) iodide ($ZnI_2$). Ferrous chloride and zinc (II) iodide are commercially available. Ferrous chloride, in particular, is more abundantly available compared to copper (I) iodide and significantly less expensive. For example, ferrous chloride and zinc (II) iodide may be obtained from Sigma-Aldrich Corp., St. Louis, Mo.

The catalyst may be provided for the reaction at a mole percent of the metal trifluoroacetate as low as about 0.5%, about 1%, about 2%, about 5%, about 10%, about 15%, about 20% or about 25%, or as high as about 30%, about 35%, about 40%, about 45%, or about 50%, or within any range defined between any two of the foregoing values, such as about 5% to about 50%, about 2% to about 45%, about 5% to about 40%, about 10% to about 35%, about 15% to about 30%, for example. Preferably, the catalyst is provided at a mole percent of the metal trifluoroacetate from about 0.5% to about 35%. More preferably, the catalyst is provided at a mole percent of the metal trifluoroacetate from about 10% to about 30%. Most preferably, the catalyst is provided at a mole percent of the metal trifluoroacetate about 25%.

The relatively low cost of ferrous chloride and zinc (II) iodide compared to copper (I) iodide, in conjunction with the lower, non-stoichiometric amounts required result in significantly more efficient and economical methods for producing trifluoroiodomethane from metal trifluoroacetates and iodine sources.

The reaction is carried out in a solvent. Solvents useful for carrying out the reaction in the liquid phase include N,N-dimethylformamide, dimethyl sulfoxide, ionic liquids, polar aprotic solvents, and combinations thereof. Examples of ionic liquids include imidazolium salts and caprolactamium hydrogen sulfate. Examples of polar aprotic solvents with high boiling points include sulfolane, N,N-dimethylacetamide, N-methyl-2-pyrrolidone (NMP), and dimethyl sulfone.

The solvent is substantially free of water. Substantially free of water means that the amount of water in the solvent is less than about 500 parts per million (ppm), about 300 ppm, about 200 ppm, about 100 ppm, about 50 ppm, about 30 ppm, about 20 ppm, or about 10 ppm, or less than any value defined between any two of the foregoing values. The foregoing ppm values are by weight of the solvent and any water. Preferably, the amount of water in the solvent is less than about 100 ppm. More preferably, the amount of water in the solvent is less than about 50 ppm. Most preferably, the amount of water in the solvent is less than about 10 ppm.

Metal trifluoroacetates are readily available in commercial quantities. For example, potassium trifluoroacetate and iodine may be obtained from Sigma-Aldrich Corp., St. Louis, Mo. The solvents may also be readily obtained in commercial quantities. For example, sulfolane may be also be obtained from Sigma-Aldrich Corp., St. Louis, Mo.

The reactants may be provided for the reaction at a mole ratio of metal trifluoroacetate to iodine source as low as about 0.1:1, about 0.2:1, about 0.3:1, about 0.4:1, about 0.5:1, about 0.6:1, about 0.7:1, about 0.8:1, about 0.9:1, about 0.95:1, about 0.99:1, or about 1:1, or as high as about 1.01:1, about 1.05:1, about 1.1:1, about 1.2:1, about 1.3:1, about 1.4:1, about 1.5:1, about 1.6:1, about 1.8:1, or about 2.0:1, or within any range defined between any two of the foregoing values, such as about 0.1:1 to about 2.0:1, about 0.5:1 to about 1.5:1, about 0.6:1 to about 1.4:1, about 0.7:1 to about 1.3:1, about 0.8:1 to about 1.2:1, about 0.9:1 to about 1.1:1, about 0.95:1 to about 1.05:1, about 0.99:1 to about 1.01:1, about 1:1 to about 2:1, about 0.8:1 to about 1.5:1, or about 0.95:1 to about 1.2:1, for example. Preferably, the mole ratio of metal trifluoroacetate to the iodine source is from about 0.8:1 to about 1.5:1. More preferably, the mole ratio of metal trifluoroacetate to the iodine source is from about 1:1 to about 1.2:1. Most preferably, the mole ratio of metal trifluoroacetate to the iodine source is about 1:1.

The reaction may be conducted a temperature as low as about 100° C., about 110° C., about 120° C., about 130° C., about 140° C., about 150° C., about 160° C., or about 170° C., or at a temperature as high as about 180° C., about 190° C., about 200° C., about 210° C., about 220° C., about 230° C., about 240° C., or about 250° C., or within any range defined between any two of the foregoing values, such as about 100° C. to about 250° C., about 110° C. to about 240° C., about 120° C. to about 230° C., about 130° C. to about 220° C., about 140° C. to about 210° C., about 150° C. to about 200° C., about 160° C. to about 190° C., about 170° C. to about 180° C., about 120° C. to about 130° C., about 110° C. to about 180° C., or about 120° C. to about 250° C., for example. Preferably, the reactants are heated to a temperature from about 100° C. to about 250° C. More preferably, the reactants are heated to a temperature from about 110° C. to about 220° C. Most preferably, the reactants are heated to a temperature of about 120° C. to about 200° C.

Pressure is not critical. Convenient operating pressures may range from about 10 KPa to about 4,000 KPa, and preferably around ambient pressure, or about 100 KPa to about 250 KPa.

The reaction is carried out in a liquid phase reactor. The liquid phase reactor may be a semi-batch or continuously stirred tank reactor (CSTR). The reaction may be carried out as a batch process or as a continuous process.

The volatile products of the reaction, including the trifluoroiodomethane, may be condensed and collected, thus separating the trifluoroiodomethane from the non-volatile metal salt byproduct.

The composition of the volatile organic products of the reaction may be measured as by gas chromatography (GC) and gas chromatography-mass spectroscopy (GC-MS) analyses. Graph areas provided by the GC analysis for each of the volatile organic compounds may be combined to provide a GC area percentage (GC area %) of the total volatile organic compounds for each of the volatile organic compounds as a measurement of the relative concentrations of the volatile organic compounds produced in the reaction.

While this invention has been described as relative to exemplary designs, the present invention may be further modified within the spirit and scope of this disclosure. Further, this application is intended to cover such departures from the present disclosure as come within known or customary practice in the art to which this invention pertains.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

EXAMPLES

Example 1

Decarboxylatiye Iodination without Catalyst

In this Example, the manufacture of trifluoroiodomethane from potassium trifluoroacetate ($CF_3COOK$) and elemental iodine is demonstrated for comparison purposes. Potassium trifluoroacetate in an amount of 20 g and elemental iodine in an amount of 38 g were added to a 300-mL reactor from Parr Instrument Company, Moline, Ill. The reactor was equipped with a condenser. The reactor was pressure tested to 300 psig, and then evacuated. Sulfolane in an amount of 60 mL was added to the reactor to form a reactant mixture having a mole ratio of potassium trifluoroacetate to elemental iodine of about 0.98:1. The reactants and the solvent were obtained from Sigma-Aldrich Corp., St. Louis, Mo and used without further purification.

The reactant mixture was heated to about 175° C. No catalyst was used in the reaction. Volatile gaseous products and byproducts were produced as the reaction proceeded. The pressure in the reactor was measured as the reaction progressed. The pressure in the reactor over time is shown in the FIGURE. The volatile gases exiting the condenser were collected in a product collection cylinder cooled in dry ice.

The composition of the organic compounds in the volatile gases collected in the product collection cylinder was measured by gas chromatography (GC). Graph areas provided by the GC analysis for each of the organic compounds were combined to provide a GC area percentage (GC area %) of the total organic compounds for each of the organic compounds as a measurement of the relative concentrations of the organic compounds. The results are shown in the Table below.

Example 2

Decarboxylatiye Iodination using a CuI Catalyst

In this Example, the manufacture of trifluoroiodomethane from potassium trifluoroacetate ($CF_3COOK$) and elemental iodine in the presence of a copper (I) iodide (CuI) catalyst is demonstrated for comparison purposes. Potassium trifluoroacetate in an amount of 20 g, copper (I) iodide in an amount of 6.2 g (25 mol %) and iodine ($I_2$) in an amount of 36.7 g were added to a 300-mL reactor from Parr Instrument Company, Moline, Ill. The reactor was equipped with a condenser. The reactor was pressure tested to 300 psig, and then evacuated. Sulfolane in an amount of 60 mL was added to the reactor to form a reactant mixture having a mole ratio of potassium trifluoroacetate to elemental iodine of about 0.91:1. The reactants and the solvent were obtained from Sigma-Aldrich Corp., St. Louis, Mo. and used without further purification. The copper (I) iodide, in powder form, was obtained from Sigma-Aldrich Corp., St. Louis, Mo. and used without further purification.

The reactant mixture was heated to about 175° C. Volatile gaseous products and byproducts were produced as the reaction proceeded. The pressure in the reactor was measured as the reaction progressed. The pressure in the reactor over time is shown in the FIGURE. The volatile gases exiting the condenser were collected in a product collection cylinder cooled in dry ice.

The composition of the organic compounds in the volatile gases collected in the product collection cylinder was measured by gas chromatography (GC). Graph areas provided by the GC analysis for each of the organic compounds were combined to provide a GC area percentage (GC area %) of the total organic compounds for each of the organic compounds as a measurement of the relative concentrations of the organic compounds. The results are shown in the Table below.

Example 3

Decarboxvlative Iodination using an $FeCl_2$ Catalyst

In this Example, the manufacture of trifluoroiodomethane from potassium trifluoroacetate ($CF_3COOK$) and elemental iodine in the presence of a ferrous chloride ($FeCl_2$) catalyst is demonstrated. Potassium trifluoroacetate in an amount of 20 g, ferrous chloride in an amount of 4.2 g (25 mol %), and iodine ($I_2$) in an amount of 36.7 g were added to a 300-mL reactor from Parr Instrument Company, Moline, Ill. The reactor was equipped with a condenser. The reactor was pressure tested to 300 psig, and then evacuated. Sulfolane in an amount of 60 mL was added to the reactor to form a reactant mixture having a mole ratio of potassium trifluoroacetate to elemental iodine of about 0.91:1. The reactants and the solvent were obtained from Sigma-Aldrich Corp., St. Louis, Mo. and used without further purification. Ferrous chloride, in powder form, was obtained from Sigma-Aldrich Corp., St. Louis, Mo. and used without further purification.

The reactant mixture was heated to about 175° C. Volatile gaseous products and byproducts were produced as the reaction proceeded. The volatile gases exiting the condenser were collected in a product collection cylinder cooled in dry ice.

The composition of the organic compounds in the volatile gases collected in the product collection cylinder was measured by gas chromatography (GC). Graph areas provided by the GC analysis for each of the organic compounds were combined to provide a GC area percentage (GC area %) of the total organic compounds for each of the organic compounds as a measurement of the relative concentrations of the organic compounds. The results are shown in the Table below.

As shown in the Table below, the use of a ferrous chloride catalyst results in higher selectivity for trifluoroiodomethane with reduced production of the byproduct trifluoromethane ($CHF_3$) when compared to the reaction run with no catalyst or with copper(I) iodide as the catalyst. As shown in the FIGURE, the ferrous chloride catalyst promoted the reaction to an extent comparable to that of the copper (I) iodide catalyst. The potassium trifluoroacetate is hygroscopic and readily absorbs moisture from the surrounding. The formation of $CHF_3$ is attributed to the presence of moisture in the reaction vessel from the potassium trifluoroacetate.

TABLE

| Catalyst | $CF_3I$ (GC area %) | $CHF_3$ (GC area %) | Other (GC area %) |
| --- | --- | --- | --- |
| none | 62.85% | 35.35% | 1.79% |
| CuI | 75.61% | 22.20% | 2.19% |
| $FeCl_2$ | 76.25% | 19.86% | 3.89% |

ASPECTS

Aspect 1 is a process for producing trifluoroiodomethane ($CF_3I$), the process comprising providing a metal trifluoroacetate, an iodine source, a metal catalyst and a solvent; and reacting the metal trifluoroacetate, the iodine source, and the metal catalyst in the presence of the solvent to produce trifluoroiodomethane, wherein the metal catalyst includes at least one selected from the group of ferrous chloride and zinc (II) iodide.

Aspect 2 is the process of Aspect 1, wherein in the providing step, a mole ratio of the metal trifluoroacetate to the iodine source is from about 0.1:1 to about 2.0:1.

Aspect 3 is the process of Aspect 1, wherein in the providing step, a mole ratio of the metal trifluoroacetate to the iodine source is from about 0.8:1 to about 1.5:1.

Aspect 4 is the process of Aspect 1, wherein in the providing step, a mole ratio of the metal trifluoroacetate to the iodine source is from about 1.1:1 to about 1.2:1.

Aspect 5 is the process of Aspect 1, wherein in the providing step, a mole ratio of the metal trifluoroacetate to the iodine source is about 1:1.

Aspect 6 is the process of any of Aspects 1-5, wherein in the providing step, the catalyst may be provided for the reaction at a mole percent of the metal trifluoroacetate of from about 0.5% to about 50%.

Aspect 7 is the process of any of Aspects 1-5, wherein in the providing step, the catalyst may be provided for the reaction at a mole percent of the metal trifluoroacetate of from about 0.5% to about 35%.

Aspect 8 is the process of any of Aspects 1-5, wherein in the providing step, the catalyst may be provided for the reaction at a mole percent of the metal trifluoroacetate of from about 10% to about 30%.

Aspect 9 is the process of any of Aspects 1-5, wherein in the providing step, the catalyst may be provided for the reaction at a mole percent of the metal trifluoroacetate of from about 20% to about 30%.

Aspect 10 is the process of any of Aspects 1-9, wherein in the providing step, the metal trifluoroacetate is at least one selected from the group of lithium trifluoroacetate, potassium trifluoroacetate, sodium trifluoroacetate, calcium trifluoroacetate, and magnesium trifluoroacetate.

Aspect 11 is the process of any of Aspects 1-9, wherein in the providing step, the metal trifluoroacetate is selected from the group consisting of lithium trifluoroacetate, potassium trifluoroacetate, sodium trifluoroacetate, calcium trifluoroacetate, magnesium trifluoroacetate, and combinations thereof.

Aspect 12 is the process of any of Aspects 1-9, wherein in the providing step, the metal trifluoroacetate is at least one selected from the group of potassium trifluoroacetate and sodium trifluoroacetate.

Aspect 13 is the process of any of Aspects 1-9, wherein in the providing step, the metal trifluoroacetate consists of potassium trifluoroacetate.

Aspect 14 is the process of any of Aspects 1-13, wherein in the providing step, the iodine source is at least one selected from the group of iodine, iodine monochloride, and iodine pentafluoride.

Aspect 15 is the process of Aspect 14, wherein the iodine source consists of iodine monochloride.

Aspect 16 is the process of Aspect 14, wherein the iodine source consists of iodine.

Aspect 17 is the process of any of Aspects 1-16, wherein in the providing step, the organic solvent comprises less than about 500 ppm by volume of water.

Aspect 18 is the process any of Aspects 1-16, wherein in the providing step, the organic solvent comprises less than about 100 ppm by volume of water.

Aspect 19 is the process any of Aspects 1-16, wherein in the providing step, the organic solvent comprises less than about 50 ppm by volume of water.

Aspect 20 is the process any of Aspects 1-16, wherein in the providing step, the organic solvent comprises less than about 10 ppm by volume of water.

Aspect 21 is the process of any of Aspects 25-40, wherein in the providing step, the organic solvent is at least one selected from the group of an ionic liquid and a polar aprotic solvent.

Aspect 22 is the process of Aspect 21, wherein the organic solvent is at least one selected from the group of imidazolium salts, caprolactamium hydrogen sulfate, sulfolane, N,N-dimethylacetamide, N-methyl-2-pyrrolidone (NMP), and dimethyl sulfone.

Aspect 23 is the process of Aspect 22, wherein the organic solvent consists of sulfolane.

Aspect 24 is the process of any of Aspects 1-23, wherein the metal catalyst comprises ferrous chloride.

Aspect 25 is the process of any of Aspects 1-23, wherein the metal catalyst consists of ferrous chloride.

Aspect 26 is the process of any of Aspects 1-23, wherein the metal catalyst comprises zinc (II) iodide.

Aspect 27 is the process of any of Aspects 1-23, wherein the metal catalyst consists of zinc (II) iodide.

Aspect 28 is the process of any of Aspects 1-27, wherein in the reacting step, the metal trifluoroacetate, the iodine source, and the solvent are at a temperature from 100° C. to 250° C.

Aspect 29 is the process of any of Aspects 1-27, wherein in the reacting step, the metal trifluoroacetate, the iodine source, and the solvent are at a temperature from about 100° C. to about 250° C.

Aspect 30 is the process of any of Aspects 1-27, wherein in the reacting step, the metal trifluoroacetate, the iodine source, and the solvent are at a temperature from about 110° C. to about 220° C.

Aspect 31 is the process of any of Aspects 1-27, wherein in the reacting step, the metal trifluoroacetate, the iodine source, and the solvent are at a temperature from about 120° C. to about 200° C.

Aspect 32 is the process for producing trifluoroiodomethane ($CF_3I$), the process comprising mixing a metal trifluoroacetate, an iodine source, a metal catalyst, and a solvent; and heating the metal trifluoroacetate, the iodine source, the metal catalyst, and the solvent to react the metal trifluoroacetate and iodine source to produce trifluoroiodomethane and a metal salt, wherein the metal catalyst includes at least one selected from the group of ferrous chloride and zinc (II) iodide.

Aspect 33 is the process of Aspect 32, further including separating the trifluoroiodomethane from the metal salt.

Aspect 34 is the process of either of Aspects 32 or 33, wherein the process is a continuous process.

Aspect 35 is the process of either of Aspects 32 or 33, wherein the process is a batch process.

Aspect 36 the process of any of Aspects 32-35, wherein a mole ratio of the metal trifluoroacetate to the iodine source is from about 0.1:1 to about 2.0:1.

Aspect 37 is the process of Aspect 1, wherein a mole ratio of the metal trifluoroacetate to the iodine source is from about 0.8:1 to about 1.5:1.

Aspect 38 is the process of Aspect 1, wherein a mole ratio of the metal trifluoroacetate to the iodine source is from about 1.1:1 to about 1.2:1.

Aspect 39 is the process of Aspect 1, wherein a mole ratio of the metal trifluoroacetate to the iodine source is about 1:1.

Aspect 40 is the process of any of Aspects 1-5, wherein the catalyst may be provided for the reaction at a mole percent of the metal trifluoroacetate of from about 0.5% to about 50%.

Aspect 41 is the process of any of Aspects 1-5, wherein the catalyst may be provided for the reaction at a mole percent of the metal trifluoroacetate of from about 0.5% to about 35%.

Aspect 42 is the process of any of Aspects 1-5, wherein the catalyst may be provided for the reaction at a mole percent of the metal trifluoroacetate of from about 10% to about 30%.

Aspect 43 is the process of any of Aspects 1-5, wherein the catalyst may be provided for the reaction at a mole percent of the metal trifluoroacetate of from about 20% to about 30%.

Aspect 44 is the process of any of Aspects 1-9, wherein the metal trifluoroacetate is at least one selected from the group of lithium trifluoroacetate, potassium trifluoroacetate, sodium trifluoroacetate, calcium trifluoroacetate, and magnesium trifluoroacetate.

Aspect 45 is the process of any of Aspects 1-9, wherein the metal trifluoroacetate is at least one selected from the group of lithium trifluoroacetate, potassium trifluoroacetate, sodium trifluoroacetate, calcium trifluoroacetate, and magnesium trifluoroacetate.

Aspect 46 is the process of any of Aspects 1-9, wherein the metal trifluoroacetate is a least one selected from the group of potassium trifluoroacetate, and sodium trifluoroacetate.

Aspect 47 is the process of any of Aspects 1-9, wherein the metal trifluoroacetate consists of potassium trifluoroacetate.

Aspect 48 is the process of any of Aspects 1-13, wherein the iodine source is at least one selected from the group of iodine, iodine monochloride, and iodine pentafluoride.

Aspect 49 is the process of Aspect 14, wherein the iodine source consists of iodine monochloride.

Aspect 50 is the process of Aspect 14, wherein the iodine source consists of iodine.

Aspect 51 is the process of any of Aspects 1-16, wherein the organic solvent comprises less than about 500 ppm by volume of water.

Aspect 52 is the process any of Aspects 1-16, wherein the organic solvent comprises less than about 100 ppm by volume of water.

Aspect 53 is the process any of Aspects 1-16, wherein the organic solvent comprises less than about 50 ppm by volume of water.

Aspect 54 is the process any of Aspects 1-16, wherein the organic solvent comprises less than about 10 ppm by volume of water.

Aspect 55 is the process of any of Aspects 25-40, wherein the organic solvent is at least one selected from the group of an ionic liquid and a polar aprotic solvent.

Aspect 56 is the process of Aspect 21, wherein the organic solvent is at least one selected from the group of imidazolium salts, caprolactamium hydrogen sulfate, sulfolane, N,N-dimethylacetamide, N-methyl-2-pyrrolidone (NMP), and dimethyl sulfone.

Aspect 57 is the process of Aspect 22, wherein the organic solvent consists of sulfolane.

Aspect 58 is the process of any of Aspects 1-23, wherein the metal catalyst comprises ferrous chloride.

Aspect 59 is the process of any of Aspects 1-23, wherein the metal catalyst consists of ferrous chloride.

Aspect 60 is the process of any of Aspects 1-23, wherein the metal catalyst comprises zinc (II) iodide.

Aspect 61 is the process of any of Aspects 1-23, wherein the metal catalyst consists of zinc (II) iodide.

Aspect 62 is the process of any of Aspects 1-27, wherein the metal trifluoroacetate, the iodine source, and the solvent are heated to a temperature from 100° C. to 250° C.

Aspect 63 is the process of any of Aspects 1-27, wherein the metal trifluoroacetate, the iodine source, and the solvent are heated to a temperature from about 100° C. to about 250° C.

Aspect 64 is the process of any of Aspects 1-27, wherein the metal trifluoroacetate, the iodine source, and the solvent are heated to a temperature from about 110° C. to about 220° C.

Aspect 65 is the process of any of Aspects 1-27, wherein the metal trifluoroacetate, the iodine source, and the solvent are heated to a temperature from about 120° C. to about 200° C.

What is claimed is:

1. A process for producing trifluoroiodomethane ($CF_3I$), the process comprising:
providing a metal trifluoroacetate, an iodine source, a metal catalyst and a solvent; and
reacting the metal trifluoroacetate, the iodine source, and the metal catalyst in the presence of the solvent to produce trifluoroiodomethane, wherein the metal catalyst includes at least one selected from the group of ferrous chloride and zinc (II) iodide.

2. The process of claim 1, wherein in the providing step, a mole ratio of the metal trifluoroacetate to the iodine source is from about 0.1:1 to about 2.0:1.

3. The process of claim 1, wherein in the providing step, the catalyst may be provided for the reaction at a mole percent of the metal trifluoroacetate of from about 0.5% to about 50%.

4. The process of claim 1, wherein in the providing step, the metal trifluoroacetate is selected from the group of lithium trifluoroacetate, potassium trifluoroacetate, sodium trifluoroacetate, calcium trifluoroacetate, magnesium trifluoroacetate, and combinations thereof.

5. The process of claim 1, wherein in the providing step, the iodine source is selected from the group of iodine, iodine monochloride, iodine pentafluoride, and combinations thereof.

6. The process of claim 1, wherein in the providing step, the solvent comprises less than about 500 ppm by volume of water.

7. The process of claim 1, wherein in the providing step, the solvent is selected from the group of an ionic liquid, a polar aprotic solvent, and combinations thereof.

8. The process of claim 7, wherein the solvent is selected from the group of imidazolium salts, caprolactamium hydrogen sulfate, sulfolane, N,N-dimethylacetamide, N-methyl-2-pyrrolidone (NMP), dimethyl sulfone, and combinations thereof.

9. The process of claim 8, wherein the solvent consists of sulfolane.

10. The process of claim 1, wherein the metal catalyst comprises ferrous chloride.

11. The process of claim 1, wherein in the reacting step, the metal trifluoroacetate, the iodine source, and the solvent are at a temperature from about 100° C. to about 250° C.

12. A process for producing trifluoroiodomethane ($CF_3I$), the process comprising:
mixing a metal trifluoroacetate, an iodine source, a metal catalyst, and a solvent; and
heating the metal trifluoroacetate, the iodine source, the metal catalyst, and the solvent to react the metal trifluoroacetate and iodine source to produce trifluoroiodomethane and a metal salt, wherein the metal catalyst includes at least one selected from the group of ferrous chloride and zinc (II) iodide.

13. The process of claim 12, further including separating the trifluoroiodomethane from the metal salt.

14. The process of claim 12, wherein the process is a continuous process.

15. The process of claim 12, wherein the process is a batch process.

16. The process of claim 12, wherein the metal trifluoroacetate is selected from the group of lithium trifluoroacetate, potassium trifluoroacetate, sodium trifluoroacetate, calcium trifluoroacetate, magnesium trifluoroacetate, and combinations thereof.

17. The process of claim 12, wherein the solvent is selected from the group of an ionic liquid, a polar aprotic solvent, and combinations thereof.

18. The process of claim 17, wherein the solvent is selected from the group of imidazolium salts, caprolactamium hydrogen sulfate, sulfolane, N,N-dimethylacetamide, N-methyl-2-pyrrolidone (NMP), dimethyl sulfone, and combinations thereof.

19. The process of claim 12, wherein in the metal catalyst comprises ferrous chloride.

20. The process of claim 12, wherein in the reacting step, the metal trifluoroacetate, the iodine source, and the solvent are at a temperature from about 100° C. to about 250° C.

* * * * *